US008784313B2

(12) United States Patent
Mebazaa et al.

(10) Patent No.: US 8,784,313 B2
(45) Date of Patent: Jul. 22, 2014

(54) METHOD OF PROGNOSIS ASSOCIATED WITH CASES OF POSTPARTUM HEMORRHAGE

(75) Inventors: Alexandre Mebazaa, Montrouge (FR); Etienne Gayat, Paris (FR); Matthieu Resche-Rigon, Paris (FR); Olivier Morel, Paris (FR); Yann Fargeaudou, Paris (FR); Matthias Rossignol, Paris (FR); Didier Payen, Paris (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 622 days.

(21) Appl. No.: 13/057,633

(22) PCT Filed: Aug. 6, 2009

(86) PCT No.: PCT/EP2009/060240
§ 371 (c)(1),
(2), (4) Date: May 31, 2011

(87) PCT Pub. No.: WO2010/015690
PCT Pub. Date: Feb. 11, 2010

(65) Prior Publication Data
US 2013/0190585 A1    Jul. 25, 2013

(30) Foreign Application Priority Data

Aug. 6, 2008 (FR) ..................... 08 55454

(51) Int. Cl.
*A61B 5/00* (2006.01)

(52) U.S. Cl.
USPC ........................................ 600/371

(58) Field of Classification Search
None
See application file for complete search history.

(56) References Cited

PUBLICATIONS

Bakshi et al., Indications for and outcomes of emergency peripartum hysterectomy. A five year review, 45(9) The Journal of Reproductive Medicine, 733-737 (Sep. 2000).
Crane et al., Maternal complication with placenta previa, 17(2) Am. J of Perinatology, 101-105 (2000).
Ducarme et al., Prise en charge chirurgicale des hémorragies de la deliverance: étude rétrospective, 35(12) Gynécologie Obstétrique & Fertilité, Éditions Scientifiques et médicales, 1209-1214 (Nov. 26, 2007).
Romano et al., The point of No Return in Post-Partum Haemorrhage, 20(2) Italian Journal of Gynaecology & Obstetrics, 112-118 (Apr. 1, 2008).
Sergent et al., Surgical management of intractable postpartum haemorrhages, 131(4) Ann. Chir., 236-43 (2006).
International Search Report corresponding to PCT/EP 2009/060240 mailed Oct. 16, 2009.

*Primary Examiner* — Michael Kahelin
*Assistant Examiner* — Mitchell Alter
(74) *Attorney, Agent, or Firm* — Buchanan Ingersoll & Rooney PC

(57) ABSTRACT

Novel prognosis methods associated with cases of postpartum haemorrhage providing a predictive test enabling practitioners to provide better management of patients suffering from postpartum haemorrhage. Different risk factors exist on which a score allowing prediction of the need to carry out invasive procedures to stop bleeding has been developed.

8 Claims, 1 Drawing Sheet

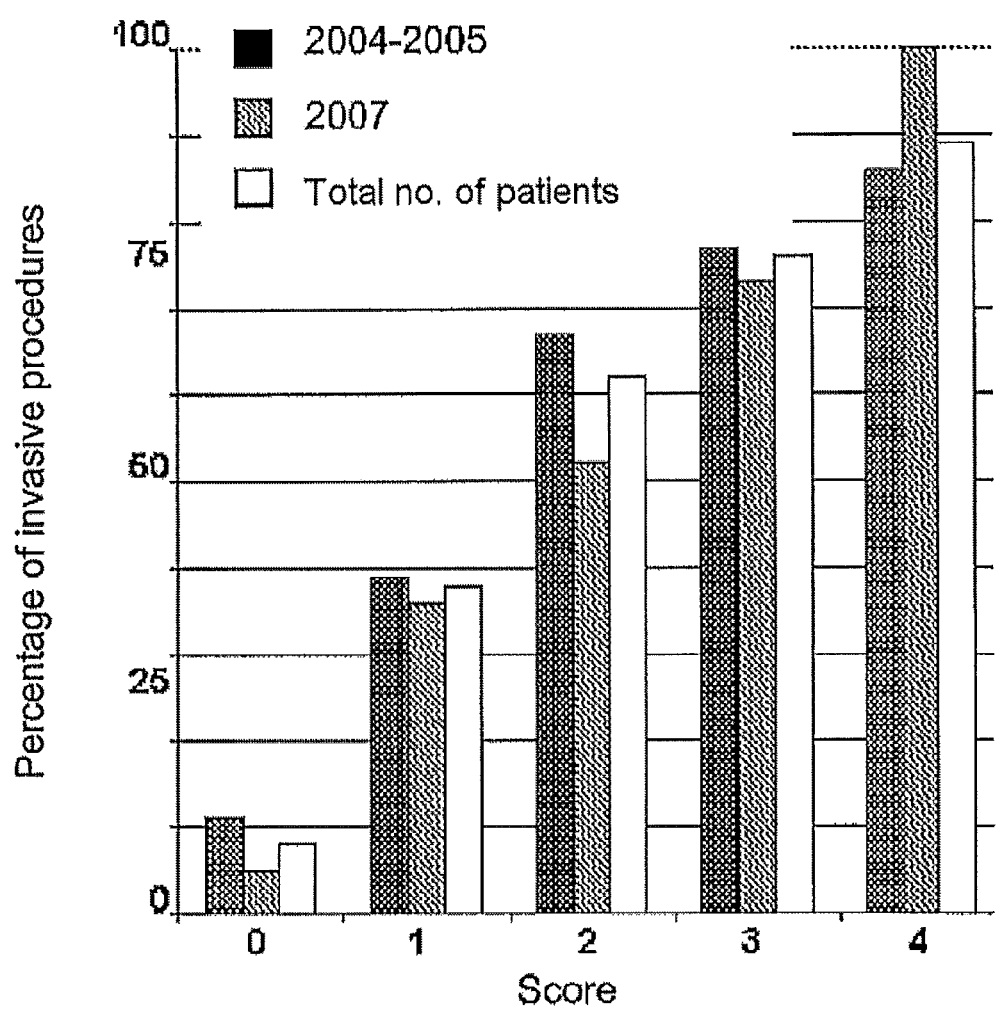

METHOD OF PROGNOSIS ASSOCIATED WITH CASES OF POSTPARTUM HEMORRHAGE

The present invention concerns a novel prognosis method associated with cases of postpartum haemorrhage.

Post-partum haemorrhage, which is defined as the loss of more 500 ml of blood after giving birth, is still seen in nearly 18% of births. The annual incidence of postpartum haemorrhage is therefore 14 million cases across the world; these being the cause of 124,000 maternal deaths. In France, the annual incidence of these haemorrhages is 70,000 to 80,000 cases which are responsible for nearly 250 deaths. In this respect, a French report explains that nearly 75% of these deaths involve failed management regarding recommended practice, notably integrating the time before transfusion, haemostatic procedure, etc.

However, since the causes of these haemorrhages are multiple, it is difficult at the present time to define a management protocol which could limit mortality arising after postpartum haemorrhage.

There is therefore an urgent need to develop a predictive test enabling practitioners to provide better management of patients suffering from post-partum haemorrhage.

After an exhaustive analysis of different cohorts of parturients who had suffered postpartum haemorrhage, the inventors have evidenced the existence of different risk factors on which they have developed a score allowing prediction of the need to carry out invasive procedure to stop bleeding.

Therefore, a first object of the invention is an in vitro method for the prognosis of halted bleeding in a patient suffering from postpartum haemorrhage without any invasive procedure, which comprises the following steps:
  a) determining, from a biological sample of said patient, the plasma fibrinogen concentration, blood tropinin concentration and prothrombin time;
  b) examining at least two clinical markers of said patient, chosen from the group consisting of heart rate and the presence of placental anomalies;
  c) calculating a score Z using the following formula: $Z = a + b + c + d + e$,
    i) where a is associated with the existence of placental anomalies in said patient, with a having a value of 0 when no anomaly of placentation is observed in said patient, and a having a value of 1 when one or more placentation anomalies are observed in said patient;
    ii) where b is associated with the heart rate of said patient, with b having a value of 0 when said patient's heart rate is less than or equal to 115 bpm (beats per minute) and b has a value of 1 when the heart rate is higher than 115 bpm;
    iii) where c is associated with the plasmatic fibrinogen concentration of said patient, with c having a value of 0 when said level is equal to or higher than 2 g/L, and with c having a value of 1 when said level is lower than 2 g/L;
    iv) where d is associated with the blood troponin concentration of said patient, d having a value of 0 if said concentration is lower than the detection threshold, and with d having a value of 1 when said concentration is higher than or equal to this same detection threshold;
    v) where e is associated with the prothrombin time (PT) of said patient, e having a value of 0 if said prothrombin time is higher than or equal to 50%, and e having a value of 1 if said prothrombin time is less than 50%;

wherein a Z score of 2 or more than 2 is indicative of the necessity to carry out invasive procedure to stop bleeding in said patient suffering from postpartum haemorrhage.

The inventors have effectively evidenced that a score of 2 or higher is associated with a probability of more than 70% of the need for invasive procedure. More specifically, the inventors have evidenced that a score of 2 is associated with a probability of nearly 50% of the need for invasive procedure, a score of 3 is associated with a probability of more than 75% and finally a score of 4 is associated with a probability of the order 90% of the need for invasive procedure.

Finally, the method developed by the inventors allows the simple and highly sensitive determining of those patients suffering from post-partum haemorrhage who will need invasive procedure to stop bleeding, so that it is possible to envisage patient management that is prompt and best adapted.

Preferably, by "biological sample" is meant a blood sample.

By "fibrinogen" or "I factor" is meant a glycoprotein of blood plasma which converts to fibrin under the action of thrombin when the blood coagulates. This glycoprotein is soluble and has a normal concentration in human plasma of between 1.8 and 4.0 g/L. The plasma concentration of fibrinogen can be simply determined using measurement methods well known to the person skilled in the art. As an example of method for measuring fibrinogen concentration, mention may be made of the ELISA method such as used in the STA FIBRINOGEN kit (DIAGNOSTICA STAGO).

By "troponin" is meant a protein complex acting in the sensitization of muscle cells to calcium.

By "detection threshold" and for troponin, is meant a concentration higher than the detectable concentration for the method used. For example, by detection threshold is generally meant a value of 1 pg/L, preferably 10 pg/L and further preferably 0.02 ng/L.

Therefore, d has a value of 0 when said concentration is lower than 1 pg/L, preferably lower than 10 pg/L, and most preferably lower than 0.02 ng/L.

Preferably, the troponin is troponin I.

BY "Troponin I" or "TnI" is meant the protein sub-unit responsible for the inhibition of binding between myosin and actin (by masking the actin site used for binding with myosin).

Further preferably, said troponin I is cardiac troponin I (SEQ ID NO:1) which has an inhibitory function allowing the triggering of muscle relaxation.

Troponin, and notably troponin I, is normally not found in the blood, detection thereof in the blood being the result of stress, and its normal blood level is to be considered zero. The detection of troponin or troponin I can be performed using methods well known to the person skilled in the art. For example, particular mention may be made of immunofluorescence using the STAT Troponin-I kit (Architect 1.2000SR Abbott), TROPONIN I ELISA kit (CALBIOTECH), or CLEARVIEW TROPONIN I (INVERNESS MEDICAL INTERNATIONAL).

By "prothrombin time" or "TP", sometimes called "Quick time" reference is made to the coagulation time of a citrated blood plasma in the presence of an extract of human, animal or synthetic tissue called thromboplastin, cytozyme or thrombokinase which comprises a set of enzymes required for blood coagulation and allows the conversion of prothrombin to thrombin. More specifically, Quick time corresponds to this measured coagulation time expressed in seconds relative to the time obtained for a control plasma (the mean of around fifty normal patients) and the prothrombin time corresponds to a percentage value obtained by plotting the Quick time obtained for the plasma being tested on Thivolle's straight line (obtained by testing successive dilutions of a normal control plasma). For example, the prothrombin time of normal plasma by definition is 100%, that of normal plasma diluted to one half is 50%, and this prothrombin time normally lies between 70 and 100%.

This prothrombin time can be measured simply using very numerous kits or apparatus available on the market such as the kits STA NEOPLASTINE (DIAGNOSTICA STAGO) or IMMEDIA™ PT System (FARALLON MEDICAL).

However, this prothrombin level has the major defect of varying according to the reagent used, which is why it is preferred to use the INR (International Normalized Ratio) for the comparison of repeated measurements in one same patient. The INR uses no unit but takes into account the sensitivity of the thromboplastin reagent according to an internationally determined index. For example, a prothrombin time of less than 50% corresponds to an INR score of more than 1.6 (for PT measured using the STA NEOPLASTINE kit (DIAGNOSTICO STAGO).

By "placentation anomalies" is meant an anomaly of placenta insertion. As examples of placentation anomalies mention may be made of placenta praevia, placenta accreta, placenta increta and placenta percreta.

Placenta praevia is characterized by low insertion of the placenta (lower segment of the uterus) which therefore partly or fully obstructs the natural birth canal, amounting to a mechanical obstacle to giving birth via vaginal route.

With placenta accreta, the placenta pathologically adheres to the wall of the uterine cavity, in this anomaly, the decidua disappears and the trophoblastic villi attach themselves directly onto the muscle layer of the uterine wall (myometrium). Depending upon the extent of penetration of the placental trophoblastic villi into the myometrium, three degrees of seriousness are described:

placenta accreta: the invasion of the trophoblastic villi is limited to the surface layer of the myometrium;
placenta increta: the trophoblastic villi penetrate into the thickness of the myometrium;
placenta percreta: the trophoblastic villi pass through the entirety of the thickness of the myometrium to reach the serosa and even neighbouring organs (the bladder in particular).

By "invasive procedure" is meant haemostatic surgery or invasive arterial embolisation.

As an example of haemostatic surgery, mention may be made of hysterectomy, vascular ligature and/or intra-abdominal packing. Said operations for haemostatic surgery are notably described in the article by SERGENT et al (*Ann. Chir.*, vol. 131(4), P. 236-43, 2006).

The method according to the invention, in parallel to calculating the score, may comprise a step to determine other biological parameters such as the haemoglobin count, these parameters not being used for calculation of the score.

The present invention will now be described in more detail with the help of examples illustrating the invention but which in no way limit the scope thereof.

EXAMPLES

1) Determining a Postpartum Haemorrhage Score to Predict the Need for Invasive Procedure A cohort of 257 patients of mean age 31 years (28-35) suffering from postpartum haemorrhage was chosen, these patients having been admitted between Jan. 1, 2004 and Dec. 31, 2005 to hospital Lariboisière (Paris, France). Among these 257 patients, had already been initially admitted to hospital Lariboisière and the 227 other patients were admitted after transfer from another hospital centre after different treatments administered to reduce bleeding had failed to prove effective. The mean transfer time was 4.8 hours (3.4-7.2) during which transfer the majority of parturients (87%) were given continuous infusions of sulprostone. More specifically, 12 had already undergone a hysterectomy and 11 vessel ligature.

On their admission to the unit, the patients were taken in charge with monitoring and correction of immediate hemodynamic disorders that were life-threatening. The persistence and intensity of bleeding from the vagina and/or peritoneum were assessed by physical examination together with ultrasound investigation.

On admission, the parturients showed severe signs, with haemoglobin levels of 9.2 g/L and hematocrit levels of 27% despite transfusion of an average of two globular concentrates and one fresh frozen plasma before admission. The parturients also showed other haemorrhagic signs including tachycardia (mean heart rate of 107 bpm), coagulopathy (mean prothrombin time (PT) of 67%) and thrombocytopaenia (mean number of platelets of 118,000 per $mm^3$). The SAPS II score (Simplified Acute Physiology Score) was 18 in the 257 patients.

These first analyses showed that the main cause of postpartum haemorrhage was uterine atony (69%), lesions of the genital tract (22%) and finally placental anomalies (8%).

In relation to the results obtained, two therapeutic options could be envisaged: 1) invasive procedure to control genital bleeding including i) surgical haemostasis or ii) angiography with uterine embolisation; and 2) if neither of the above was immediately indicated since bleeding had either stopped or was minimal, the parturients were kept under observation.

After initial evaluation, 110 parturients underwent haemostatic invasive procedures due to persistent bleeding, after which the parturients were kept in the intensive care or intermediate care unit.

These procedures included 85 arterial embolisations alone (mostly uterine arteries), 14 haemostatic surgical procedures alone, and 11 embolisations and surgery combined. Haemostatic surgery (n=25) included hysterectomies, vessel ligatures and peritoneal dressings; whether or not combined. More specifically, the arterial embolisations were performed 1.9 hours (1.2-2.5) after admission, and the invasive procedures were performed 2.1 hours (1.4-4.6) after admission.

For the remainder of this analysis, the cohort of 257 patients was sub-divided into sub-groups depending on whether the patient had or had not undergone invasive procedure, invasive procedure (IP) being defined as haemostatic surgery (hysterectomy and/or vessel ligature and/or intra-abdominal packing) and/or uterine arterial embolisation. Therefore the 257 patients were subdivided into an "IP" group for those patients requiring IP, and a "medical monitoring" group (MM) which included patients who had not undergone any of the above-mentioned procedures.

For the 110 parturients in the IP group, two deaths were recorded, and the mean stay time for the other parturients in this group was 3.2 days (2.3-6.2), bleeding having been halted in all parturients and no re-admission to hospital being observed.

For the 147 parturients in the MM group, bleeding was considered as low either on admission or thereafter. There was no mortality in this group and the mean hospital stay for these patients was 0.9 day (0.65-2.1) with no subsequent readmission to hospital.

The precise characteristics of these two sub-groups compared with the cohort as a whole are detailed in following Table I.

TABLE I

|  |  | Cohort (n = 257) | MM sub-group | IP sub-group |
|---|---|---|---|---|
| Arterial embolisation (n = 96) | Single session | 96 (37%) | — | 96 (37%) |
|  | Need for 2$^{nd}$ session | 7 (2.7%) | — | 7 (2.7%) |
| Haemostatic surgery (n = 25) | Hysterectomy | 7 (2.8%) | — | 7 (2.8%) |
|  | Intra-abdominal packing | 17 (6.7%) | — | 17 (6.7%) |
|  | Vessel ligature | 6 (2.4%) | — | 6 (2.4%) |
| Severity and prognosis | SAPS II | 18 (12-24) | 15 (12-21) | 22 (16.5-32) |
|  | APACHE II | 10 (6-13) | 7 (6-11) | 12 (8-16) |
|  | Prognosis intensive care | 37 (14.4%) | 6 (4%) | 31 (28%) |
|  | Stay time (days) | 1.97 (0.8-4.0) | 0.94 (0.65-2.1) | 3.22 (2.3-6.17) |
|  | Mortality | 2 (0.8%) | 0 (0%) | 2 (1.8%) |

More specifically, the different patient parameters respectively collected prior to admission and at the time of admission are respectively given in following Tables II and III.

TABLE II

|  | Total (n = 257) | MM Group (n = 147) | IP Group (n = 110) | p value |
|---|---|---|---|---|
| Age | 31 [29-35] | 31 [27-35] | 32 [30-36] | 0.019 |
| Obstetric parameters |  |  |  |  |
| Primiparas | 109 (46) | 49 | 41 | 0.23 |
| Primigravidas | 85 (35) | 39 | 29 | 0.51 |
| Prior postpartum haemorrhage | 8 (3) | 4 | 2 | 0.48 |
| Uterine fibroma | 12 (5) | 9 (6) | 3 (3) | 0.37 |
| Scarred uterus | 30 (12) | 14 (8) | 16 (16) | 0.07 |
| Toxaemia | 30 (12) | 18 (12) | 12 (12) | 0.92 |
| Term (weeks) | 39 [37-40] | 39 [38-40] | 39 [37-40] | 0.042 |
| Twin pregnancy | 15 (6) | 7 (6) | 8 (7) | 1 |
| Birth at university hospital | 57 (22) | 25 (15) | 32 (32) | 0.0016 |
| Delivery details |  |  |  |  |
| Induced birth | 49 (20) | 37 (25) | 12 (13) | 0.034 |
| Vaginal birth | 175 (70) | 110 (75) | 65 (65) | 0.21 |
| Labour (hours) | 5 [4-8] | 6 [4-8] | 4 [2-6] | 0.016 |
| Use of instruments | 51 (21) | 33 (22) | 18 (19) | 0.63 |
| Manual removal of the placenta | 124 (49) | 71 (48) | 53 (53) | 0.31 |
| Uterine examination | 174 (70) | 106 (72) | 68 (68) | 0.57 |
| Obstetrical anaesthesia |  |  |  | 0.35 |
| General anaesthesia | 27 (10) | 13 (9) | 14 (14) |  |
| Epidural anaesthesia | 162 (65) | 98 (66) | 64 (62) |  |
| Spinal anaesthesia | 30 (12) | 18 (12) | 12 (13) |  |
| No anaesthesia | 31 (13) | 20 (14) | 11 (11) |  |
| Causes of haemorrhage |  |  |  | 0.0034 |
| Primary uterine atony | 178 (69) | 109 (74) | 69 (61) |  |
| Genital lesion | 56 (22) | 34 (23) | 22 (20) |  |
| Placental anomaly | 20 (8) | 4 (3) | 16 (14) |  |
| Uterine rupture | 3 (1) | 0 (0) | 3 (3) |  |
| Surgical procedure before transfer |  |  |  |  |
| Vaginal examination (retractor) | 90 (36) | 61 (41) | 29 (30) | 0.11 |
| Hysterectomy | 12 (5) | 4 (3) | 8 (8) | 0.079 |
| Intraabdominal packing | 5 (2) | 0 (0) | 5 (5) | 0.012 |
| Vessel ligature | 11 (4) | 7 (5) | 4 (4) | 1 |
| Medical monitoring before admission |  |  |  |  |
| Sulprostone infusion | 217 (87) | 131 (89) | 86 (85) | 0.44 |
| Catecholamine | 5 (2) | 0 (0) | 5 (5) | 0.011 |
| Mechanical ventilation | 35 (14) | 13 (9) | 22 (20) | 0.028 |
| Globular concentrate | 1.8 ± 3.2 | 1.2 ± 2.0 | 2.8 ± 4.1 | 0.00042 |
| Fresh frozen plasma | 1.0 ± 2.4 | 0.6 ± 1.7 | 1.6 ± 3.1 | 0.0026 |
| UCP | 0.2 ± 1.3 | 0.1 ± 0.4 | 0.4 ± 1.9 | 0.11 |
| Time between birth and admission (hours) | 5 [3-7] | 5 [4-7] | 4 [3-7] |  |
| Transport time (hours) | 0.5 [0.2-0.7] | 0.5 [0.2-0.7] | 0.5 [0.2-0.7] | 1 |

TABLE III

|  | Total (n = 257) | MM Group (n = 147) | IP Group (n = 110) | p value |
|---|---|---|---|---|
| Haemodynamic status |  |  |  |  |
| SAP (Systolic arterial pressure) (mmHg) | 110 [95-120] | 110 [100-120] | 100 [87-115] | 0.00069 |
| DAP (diastolic arterial pressure) (mmHg) | 55 [50-60] | 60 [50-65] | 50 [45-60] | 0.00084 |

TABLE III-continued

|  | Total (n = 257) | MM Group (n = 147) | IP Group (n = 110) | p value |
|---|---|---|---|---|
| HR (heart rate) (bpm) | 105 [90-120] | 100 [90-115] | 115 [100-130] | $1.6^e-05$ |
| Biological values | | | | |
| pH | 7.42 [7.37-7.44] | 7.43 [7.4-7.45] | 7.39 (7.32-7.43] | $1.9^e-06$ |
| PaCO$_2$ (mmHg) | 32 [29-36] | 32 [29-35] | 33 [29.25-38] | 0.1 |
| PaO$_2$ (mmHg) | 161 [110-220.8] | 138 [104-187] | 195 [144-247] | $9.1^e-06$ |
| Bicarbonate (mmol/L) | 22 [21-24] | 23 [22-24] | 22 [20-23] | $3.8^e-05$ |
| Proteins (g/L) | 42 [37-49] | 45 [40-51] | 38 [32.5-43] | $1.7^e-10$ |
| Creatinine (µmol/L) | 58 [50-69] | 57.5 [50.75-67.25] | 59 (48.5-70.5] | 0.66 |
| Lactate (mmol/L) | 2.13 [1.56-2.76] | 1.91 [1.39-2.5] | 2.5 [1.92-3.73] | $6.8^e-07$ |
| AST (IU/mL) | 22 [18-31] | 23 [19.25-30] | 21 [16-31] | 0.094 |
| ALT (IU/mL) | 13 [10-17] | 12 [10-16] | 13 [10-18] | 0.13 |
| Troponin I (ng/mL) | 0 [0-0.2] | 0 (0-0.03] | 0.06 [0-0.4] | $1.6^e-07$ |
| Bilirubine (mmol/L) | 7 [4-12] | 7 [4-11] | 8 [5-15] | 0.17 |
| Hb (g/dL) | 9.2 [7.9-10.3] | 9.5 [8.2-10.6] | 8.7 [7.0-9.9] | 0.0013 |
| Hematocrit (%) | 27 [23-30] | 27 [24-31] | 25 [20-30] | 0.00064 |
| Platelets (/mm$^3$) | 118,000 [80,250-154,000] | 130,500 [97,750-161,200] | 92,500 (63,750-133,000] | $4.5^e-05$ |
| PT (%) | 69 [55-79] | 73 [64-85] | 58.5 [38-73] | $8.7^e-09$ |
| Fibrinogen (g/L) | 2.34 [1.55-3.12] | 2.65 [2.08-3.46] | 1.8 [1.09-2.52] | $2.9^e-10$ |
| Factor V (%) | 49 [31-61] | 52 [39-66] | 41 [23-56] | 0.00057 |

The results show that, among the demographic and obstetric parameters collected prior to admission of the patients, very few differences were able to be identified between the IP and MM groups (see Table II).

Among the significant identified parameters, mention may be made of older patients, shortened term, shorter labour time, more frequent use of induced labour, weaker primary uterine atony and more placental anomalies (placenta praevia, placenta accreta and placenta percreta) in the patients of the IP group compared with the MM group. On the other hand, major differences could be observed in hemodynamic and biological measurements between the IP and MM groups on admission (see Tables II and III). The patients in the IP group showed unstable hemodynamic status with low SAP and DAP, high heart rate, low haemoglobin level, high level of plasma troponin I and metabolic acidosis despite major transfusion of red blood cells and stronger administration of catecholamine. Coagulopathy was also higher in the IP group with a low number of platelets, low PT, low level of factor V and of fibrinogen levels even though more patients had been transfused in the IP group than in the MM group.

With a view to identifying pertinent parameters to determine a predictive model for invasive procedure, these different parameters were further analyzed. Since the objective of the study was to determine at least the necessity of embolisation, intra-abdominal packing, hysterectomy or vessel ligature, a marginal association was determined between variables taken alone and prognosis using a WILCOXON test for quantitative variables and an exact FISCHER test.

For this purpose, multiple logistic regression was used to determine a set of variables independently associated with each prognosis. The variables associated with invasive procedure at a level of 0.15 and with less than 5% of missing data were taken into consideration in the multiple model. For internal clinical validity, the continuous covariables were categorised, notably systolic arterial pressure (SAP) <90 mmHg, diastolic arterial pressure (DAP) <55 mmHG, heart rate (HR) >115 beats per minute (bpm), prothrombin time (PT) <50%, fibrinogen level <2 g/L and troponin I level detectable or non-detectable.

Finally, multivariate analysis allowed the identification of 5 independent factors predictive of the IP group, which factors could be identified on admission of the patients. These factors are the following:

1) placental anomalies (OR: 7.05[2.26-22.03], p=0.0007)
2) Heart rate (HR)>115 bpm (OR: 2.18[1.03-4.62], p=0.04)
3) Prothrombin time <50% (OR: 3.55[1.38-9.17], p=0.008)
4) Fibrinogen <2 g/L (OR: 2.75(1.51-4.95], p=0.005)
5) Detectable troponin I level (OR: 2.73[1.51-4.95], p=0.0009).

Having regard to these factors, it was possible to develop a predictive score for a given patient, a value of 1 being assigned in this score for each of the above if it was observed in this patient. For a given patient, and in relation to the factors identified in this patient, a score can therefore be determined which will have a value of between 0 and 5 depending on whether or not one or more of these above-described factors are observed.

It emerged from the results obtained that a patient having a score of at least two or more carried a risk of more than 70% that invasive procedure would be necessary to stop bleeding subsequent to a postpartum haemorrhage.

2) Validation of the Predictive Model

To do so, the predictive model was tested in a new cohort of 150 patients suffering from postpartum haemorrhage and admitted throughout the year 2007. The different parameters measured on admission in this new cohort compared with the previous cohort are given in Table IV.

TABLE IV

|  | 2004/2005 Cohort (n = 257) | 2007 Cohort |
|---|---|---|
| OBSTETRICAL DETAILS | | |
| Age | 31 (29-35) | 32 (28-36) |
| Primiparas | 109 (46) | 67 (44) |
| Primigravidas | 85 (35) | 56 (37) |
| Toxaemia | 30 (12) | 15 (11) |
| Transfer from university hospital | 57 (22) | 51 (34) |
| Twin pregnancy | 15 (6) | 8 (5) |
| Term (weeks) | 39 (37-40) | 39 (38-40) |
| Delivery details | | |
| Vaginal delivery | 175 (70) | 83 (56) |
| Use of instruments | 51 (21) | 20 (14) |
| Uterine examination | 174 (70) | 83 (55) |
| Cause of haemorrhage | | |
| Primary uterine atony | 178 (69) | 110 (73) |
| Genital tract lesion | 56 (22) | 28 (19) |
| Placental anomaly | 20 (8) | 11 (7) |
| Uterine rupture | 3 (1) | 1 (1) |
| MANAGEMENT BEFORE TRANSFER | | |
| Time before transfer | 5 (3-7) | 4.8 (3.4-7.2) |
| Surgery before transfer | | |
| Examination with vaginal retractor | 90 (36) | 75 (50) |
| Hysterectomy | 12 (5) | 4 (3) |
| Vessel ligature | 11 (4) | 8 (5) |
| Medical treatment | | |
| Sulprostone infusion | 217 (87) | 141 (94) |
| Mechanical ventilation | 35 (14) | 15 (10) |
| Globular concentrate | 1.8 ± 3.2 | 2.1 ± 2.8 |
| Fresh frozen plasma | 1.0 ± 2.4 | 1.1 ± 2.3 |
| VALUES ON ADMISSION | | |
| Haemodynamic | | |
| SAP (mmHg) | 110 (95-120) | 120 (110-132) |
| DAP (mmHg) | 55 (50-60) | 70 (60-78) |
| HR (bpm) | 105 (90-120) | 100 (80-110) |
| Biological values | | |
| Troponin I (ng/mL) | 0 (0-0.2) | 0 (0-0.4) |
| Hb (g/dL) | 9.2 (7.9-10.3) | 9.0 (7.5-10.3) |
| Platelets (per mm$^3$) | 118,000 (80,250-154,000) | 130,000 (92,000-160,000) |
| PT (%) | 69 (55-79) | 67 (58-76) |
| Fibrinogen (g/L) | 2.34 (1.55-3.12) | 2.7 (1.91-3.28) |
| PATIENT MANAGEMENT AT THE CENTRE | | |
| SAPS-2 | 18 (12-24) | 13 (9.5-20) |
| Arterial embolisation | 96 (37%) | 37 (25%) |
| Second arterial embolisation | 7 (2.7%) | 2 (2%) |
| Haemostatic surgery | | |
| Hysterectomy | 7 (2.8) | 2 (1) |
| Vessel ligature | 6 (2.4) | 2 (1) |
| Stay in intensive care | 37 (14.4%) | 10 (7%) |
| Mortality | 2 (0.8%) | 0 (0%) |

The results showed that the characteristics of the 2007 cohort are similar to those of the preceding cohort, with a greater number of vaginal retractor examinations however and fewer invasive procedures than in the preceding cohort.

The previously developed score was used in this new cohort.

FIG. 1 shows the results of the score such as described in the foregoing for the 2004/2005 cohort, the 2007 cohort and for all patients taken together with respect to the risk of invasive procedure.

Finally, the results obtained gave confirmation of the high specificity of the score such as developed, as a tool predictive of the necessity for invasive procedure to stop bleeding subsequent to postpartum haemorrhage (see FIG. 1).

The invention claimed is:

1. An in vitro prognosis method for halted bleeding in a patient suffering from postpartum haemorrhage without any invasive procedure, comprising the following steps:
    a) determining with an assay apparatus the plasmatic fibrinogen concentration, troponin I blood concentration and prothrombin time from a biological sample of said patient;
    b) examining at least two clinical markers of said patient chosen from the group consisting of heart rate and the presence of placentation anomalies;
    c) calculating a Z score as per the following formula: Z=a+b+c+d+e,
        i) where a is associated with the existence of placentation anomalies in said patient, with a having a value of 0 if no placental anomaly is observed in said patient, and a having a value of 1 if one or more placentation anomalies are observed in said patient;
        ii) where b is associated with the heart rate of said patient, with b having a value of 0 if the heart rate of said patient is less than or equal to 15 bpm (beats per minute) and b having a value of 1 if the heart rate is higher than 115 bpm;
        iii) where c is associated with the plasmatic fibrinogen concentration of said patient, with c having a value of 0 if said level is equal to or higher than 2 g/L and c having a value of 1 if said level is lower than 2 g/L;
        iv) where d is associated with the blood troponin I concentration of said patient, with d having a value of 0 when said concentration is lower than 0.02 ng/L, and d having a value of 1 if said concentration is higher than or equal to 0.02 ng/L;
        v) where e is associated with the prothombin time (PT) of said patient, e having a value of 0 if said prothrombin time is higher than or equal to 50%, and e having a value of 1 if said prothrombin time is less than 50%;
    wherein a Z score higher than or equal to a value of 2 is indicative of the need to carry out invasive procedure to stop bleeding in said patient suffering from postpartum haemorrhage.

2. The method according to claim 1, characterized in that said biological sample is a blood sample.

3. The method according to claim 1, characterized in that troponin I is cardiac troponin I.

4. The method according to claim 1, characterized in that d has a value of 0 if the blood troponin I concentration is lower than 1 pg/L.

5. The method according to claim 1, characterized in that the placentation anomalies are chosen from the group consisting of placenta praevia, placenta accreta, placenta increta, and placenta percreta.

6. The method according to claim 1, characterized in that said invasive procedure is haemostatic surgery or uterine arterial embolisation.

7. The method according to claim 6, characterized in that said invasive procedure is haemostatic surgery chosen from the group comprising hysterectomy, vessel ligature, and intra-abdominal packing.

8. The method according to claim 1, characterized in that d has a value of 0 if the blood troponin I concentration is lower than 10 pg/L.

* * * * *

```
SEQUENCE LISTING

<160> NUMBER OF SEQ ID NOS: 1

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80
```

```
Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
                100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
        130                 135                 140

Arg Arg Val Arg Ile Ser Ala Asp Ala Met Met Gln Ala Leu Leu Gly
145                     150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210
```